US006342065B1

(12) United States Patent
Shalaby

(10) Patent No.: US 6,342,065 B1
(45) Date of Patent: Jan. 29, 2002

(54) HIGH STRENGTH FIBERS OF L-LACTIDE COPOLYMERS ε-CAPROLACTONE AND TRIMETHYLENE CARBONATE AND ABSORBABLE MEDICAL CONSTRUCTS THEREOF

(75) Inventor: Shalaby W. Shalaby, Anderson, SC (US)

(73) Assignee: Poly-Med, Inc., Pendleton, SC (US)

(*) Notice: Subject to any disclaimer, the term of this patent is extended or adjusted under 35 U.S.C. 154(b) by 0 days.

(21) Appl. No.: 09/523,754

(22) Filed: Mar. 13, 2000

Related U.S. Application Data

(60) Provisional application No. 60/124,838, filed on Mar. 17, 1999.

(51) Int. Cl.$^7$ .......................... A61B 17/04; C08G 63/08; A61L 17/00
(52) U.S. Cl. ...................... 606/230; 606/231; 525/415; 528/354
(58) Field of Search ................................. 606/228, 230, 606/231; 528/354, 357; 424/426; 525/415

(56) References Cited

U.S. PATENT DOCUMENTS

| | | | |
|---|---|---|---|
| 4,429,980 A | 2/1984 | Miller | ...... 354/311 |
| 4,605,730 A | 8/1986 | Shalaby et al. | ...... 528/357 |
| 4,700,704 A | 10/1987 | Jamiolkowski et al. | .. 128/335.5 |
| 5,252,701 A * | 10/1993 | Jarrett et al. | ...... 528/354 |
| 5,425,984 A | 6/1995 | Kennedy et al. | ...... 428/229 |
| 5,798,436 A * | 8/1998 | Gruber et al. | ...... 528/354 |
| 5,854,383 A * | 12/1998 | Erneta et al. | ...... 528/354 |
| 5,951,997 A * | 9/1999 | Bezwada et al. | ...... 424/426 |
| 6,093,792 A * | 7/2000 | Gross et al. | ...... 528/354 |

FOREIGN PATENT DOCUMENTS

| | | | |
|---|---|---|---|
| DE | 43 00 420 A1 | 7/1994 | ...... C08G/81/00 |
| EP | 0 241 252 A2 | 10/1987 | ...... A61L/27/00 |
| EP | 0 500 098 A2 | 8/1992 | ...... C08G/63/08 |
| WO | WO 94/11441 | 5/1994 | ...... C08L/67/04 |

* cited by examiner

Primary Examiner—Gary Jackson
(74) Attorney, Agent, or Firm—Leigh P. Gregory

(57) ABSTRACT

The present invention is directed to crystalline copolymers of l-lactide and a minor portion of a cyclic monomer, preferably ε-caprolactone or trimethylene carbonate or both. The present copolymers have a melting temperature of at least 150° C. and a crystallinity of at least 25%. Preferred are high molecular weight copolymers having an inherent viscosity of at least 1.4 dl/g. A variety of surgical constructs may be formed from the present copolymers. Surgical sutures made of mono- or multifilament yarns of the present copolymers will bioabsorb in less than three years and will maintain at least 50% of their initial strength three weeks post-operatively.

14 Claims, No Drawings

HIGH STRENGTH FIBERS OF L-LACTIDE COPOLYMERS ε-CAPROLACTONE AND TRIMETHYLENE CARBONATE AND ABSORBABLE MEDICAL CONSTRUCTS THEREOF

This application claim benefit to Provisional No. 60/124,838 filed Mar. 17, 1999.

BACKGROUND TO THE INVENTION

It is well established in the prior art that absorbable fibers suitable for constructing biomedical constructs with prolonged strength retention profile, as in certain surgical sutures and meshes as well as prosthetic tendons and ligaments, need to be based on polymers having (1) high molecular weight; (2) a high degree of crystallinity; and (3) minimum or no monomeric species. These requirements were claimed to have been fulfilled by the l-lactide/glycolide copolymers described in U.S. Pat. No. 5,425,984 and EP Application No. 241,252 (1987). However, in certain high load-bearing applications where a prosthetic fibrous construct experiences cyclic stresses and is expected to maintain a substantial fraction of its initial strength for several weeks post-operatively, additional requirements are imposed. Typical examples of such constructs are surgical meshes for hernia repair and prosthetic tendons and ligaments. These additional requirements are expected to be associated with having a high degree of toughness, as measured in terms of the work required to break, without compromising, significantly, their high tensile strength, high elastic modulus, low stretchability, and high yield strength. Such requirements also are expected to be associated with a polymeric chain with higher hydrolytic stability than those containing glycolate sequences are. Unfortunately, the prior art of absorbable polymers provides conflicting teachings that may be applied towards meeting the aforementioned additional requirements. To increase toughness, the introduction of more flexible 6-caprolactone-based sequences in polyglycolide chain has been used successfully in the production of low modulus sutures (see, for example, U.S. Pat. Nos. 4,605,730 and 4,700,704) but with compromised strength. A similar situation is encountered in the copolymer of glycolide and trimethylene carbonate (see, for example. U.S. Pat. No. 4,429,980). Interestingly, fibers made of these two types of copolymers do display a lower propensity to hydrolysis than polyglycolide, but their strength loss profiles remain unsuitable for long-term, load-bearing applications. Unexpectedly, the present invention describes a copolymeric ε-caprolactone and trimethylene carbonate based compositions, which meet the above noted stringent requirement for fibers suited for the construction of biomedical devices that are expected to (1) support high loads; (2) experience cyclic stresses; (3) display minimum stretchability; (4) display a high degree of toughness; (5) display optimum hydrolytic stability; and (6) possess a prolonged strength profile, particularly during the initial post-operative period.

SUMMARY OF THE INVENTION

The present invention is directed to a crystalline copolymer which is a copolymer of l-lactide and at least one cyclic monomer which is a liquid at or above about 40° C., wherein the l-lactide derived sequences of the polymer chain comprise from about 86 to about 99 percent of all sequences, and wherein the copolymer has a $T_m$ of at least 150° C., exhibits a crystallinity of at least about 25%, and has an inherent viscosity of at least about 1.4 dl/g.

Preferably the cyclic monomer is ε-caprolactone, trimethylene carbonate, or both. Molar ratios of l-lactide to cyclic monomer which are within the scope of the present invention include 86 to 14, 87 to 13, 88 to 12, 89 to 11, 90 to 10, 91 to 9, 92 to 8, 93 to 7, 94 to 6, 95 to 5,96 to 4,97 to 3,98 to 2, and 99 to 1.

A monofilament suture made from the copolymer of the present invention has an elastic modulus of greater than about 400,000 psi, a tensile strength of greater than about 40,000 psi, and a percent elongation of less than about 50%.

Also within the scope of the present invention are multifilament yarns made from the copolymer of the present invention. Such multifilament yarns which may be employed as surgical sutures or may be formed into a surgical device or construct such as, for example, a mesh, a prosthetic tendon, a ligament or a vascular graft.

DETAILED DESCRIPTION OF PREFERRED EMBODIMENTS

The present invention is directed to high molecular weight copolymers of a major portion of l-lactide and a minor portion of ε-caprolactone (CL) or trimethylene carbonate (TMC) or both. High molecular weight is defined as displaying an inherent viscosity of at least 1.4 dl/g. The molar ratio of l-lactide to comonomer is between from about 86 to about 14 and from about 99 to about 1. Preferably, the ratio is in the range of from about 91 to about 9, more preferably from about 92 to about 8 and most preferably from about 95 to about 5. The present copolymers, particularly the l-lactide/caprolactone copolymers of the present invention, have a degree of crystallinity of greater than about 25%.

The present invention is also directed to l-lactide/caprolactone, l-lactide/trimethylene carbonate and l-lactide/caprolactone/trimethylene carbonate-based monofilament yarn having a Young's modulus of more than 400,000 psi, a tensile strength exceeding 40,000 psi, a percent elongation of less than 50%, a $T_m$ of greater than about 150° C., and a degree of crystallinity exceeding 25%. The present invention is also directed to multifilament yarn having a tenacity in excess of 3 g/d with single fiber diameter of less than 35μ. In accordance with the present invention, surgical suture made of such monofilament and multifilament yarns absorb in less than 3 years and maintain at least 50% of their initial strength at three weeks post-operatively, preferably at six weeks post-operatively. Also within the scope of the present invention are prosthetic ligaments, tendons, meshes for tissue repair, and vascular grafts made totally of such multifilament yarns or a combination the present multifilaments and monofilaments or a combination with other more absorbable multifilament or monofilament yarns.

The following Examples are representative of preferred copolymers of the present invention exemplary applications thereof.

EXAMPLE 1

Synthesis of 95/5 l-lactide/caprolactone Copolymer

In a typical reaction, l-lactide (6.67 moles, 960.5 g) and ε-caprolactone (0.35 moles, 39.9 g) were polymerized using decyl alcohol ($7.02 \times 10^{-3}$ moles, 1.11 g) as the initiator and stannous octoate ($3.51 \times 10^{-4}$ moles, 1.76 ml of 0.2 M solution in toluene) as the catalyst. The monomer to initiator ratio was 1,000 to 1; the monomer to catalyst ratio was 20,000 to 1. The reaction was carried out in a stainless steel resin kettle with a mechanical stirrer. The charge was dried under vacuum at 37° C. for 30 min. and 50° C. for 30 min. The monomer was then melted at 110° C. under positive argon pressure. Once melted, the charge was stirred at 32 rpm and heated to 140° C. After a short time at 140° C. the polymer solidified and could no longer be stirred. The polymerization was carried out for 48 hours at 140° C.

followed by 16 hours at 120° C. The resulting polymer was characterized using GPC, DSC, viscosity, and carbon and proton NMR. The results for the three polymer lots made by this general method are summarized in Table I.

EXAMPLE 2

General Method of Monofilament Spinning

Prior to extrusion, the polymer is first heated under vacuum (about 0.1 mm Hg) for at least 12 hours at 37° C. and then at 80° C. for 8 hours. The dried polymer is transferred to a hopper protected with an argon blanket attached to a 0.5 inch extruder. The temperature setting at zones 1, 2, 3, and the die can be adjusted to 130–160° C., 170–195° C., 190–220° C., and 195–220° C., respectively, depending on the polymer molecular weight. The screw speed can be adjusted at 15–40 rpm depending on the polymer viscosity and extent of jet-stretching. The extrudate is quenched in air or an ice-water bath before winding. The wound extrudate is then dried under vacuum at 25° C. for 6 hours and then at 37° C. for 12 hours before drawing.

EXAMPLE 3

Extrusion of 95/5 l-lactide/caprolactone Copolymer

Prior to extrusion, the polymer of Example 1 was ground and dried under vacuum at 37° C. for at least 12 hours and then at 80° C. for 8 hours. The polymer was extruded using a Microtruder from Randcastle at the following typical settings: zone 1 T=155° C.; zone 2 T=190° C.; zone 3 T=195° C.; screw speed=27.8 rpm. The extruded monofilaments were characterized using solution viscometry and DSC. Relevant data are shown in Table II.

EXAMPLE 4

General Method for Monofilament Yarn Orientation

The orientation of the monofilament can be achieved by drawing in two stages using a heated glycerin bath or convection oven. The first and second stages can be achieved at 90–105° C. and 105–120° C. to provide 4–4.5 X and 1.25–1.5 X draw-ratios, respectively. The drawing conditions depend on the polymer molecular weight and desired elongation to break.

EXAMPLE 5

Orientation of 95/5 l-lactide/caprolactone Copolymer

The extruded monofilaments of Example 3 were stored under vacuum prior to drawing. Single stage drawing of the monofilament was accomplished at, for example, a temperature of 75° C. and a draw ratio of 2.4 (Table III-A). The drawn fibers were tested in tension to determine their strength, modulus, and percent elongation at break. Relevant data of partially oriented monofilaments are shown in Table III-B. The tensile properties of two-stage drawn monofilaments (at 70° C. and 85° C. using draw ratios of 4.3, 6.7, and 8.0) are summarized in Table IV.

Comparative Example 6

Synthesis of 95/5 -lactide/glycolide Copolymer

The copolymer of the present Example was prepared under conditions similar to those used in Example 1, but substituting glycolide for ε-caprolactone. Two further lots of this copolymer were prepared as outlined in Table I. Other relevant data are summarized in Table I.

Comparative Example 7

Extrusion of 95/5 l-lactide/glycolide Copolymer

The copolymer of Example 6 was extruded under similar conditions to those used in example 3. Relevant data are summarized in Table II.

Comparative Example 8

Orientation of 95/5 l-lactide/glycolide Copolymer

The extrudate of Example 7 was oriented under similar conditions to those used in Example 5. Relevant data are summarized in Table III.

EXAMPLE 9

Synthesis of 95/5 l-lactide/ε-caprolactone Copolymer

The reaction apparatus was comprised of a 1L stainless steel kettle with a 3-neck glass lid equipped with an overhead mechanical stirring unit, vacuum adapter, and two 90° C. for an argon inlet. After obtaining a vacuum of 0.2 mm Hg, the apparatus was flame dried. An initial charge of 1152.2 grams (8 moles) l-lactide was added to the kettle.

The apparatus and its contents were placed under room temperature vacuum for 1 hour. Using a high temperature oil bath, the apparatus and its contents were heated to 40° C. and kept under vacuum for 3 hours. The system was then purged with argon. The temperature of the oil bath was increased to 110° C. and stirring initiated at 32 rpm. After 1 hour and 50 minutes, the temperature was increased to 120° C. Upon complete melting of the contents after 45 minutes, a final charge consisting of 48.1 grams (0.421 moles) εcaprolactone. 1.61 milliliters ($8.421 \times 10^{-3}$ moles) decyl alcohol, and 2.11 milliliters ($4.21 \times 10^{-4}$ moles) of a 0.2M solution of stannous octoate catalyst in toluene was added to the kettle while stirring. After 15 minutes, the temperature was increased to 140° C. and stirring was stopped. The reaction was maintained at 140° C. for 48 hours. after which time the temperature was decreased to 120° C. and maintained for 16 hours. At the conclusion of this period, the polymer was isolated, ground, and heated under reduced pressure (about 0.1 mm Hg) at 37° C. for 4 hours and 80° C. for at least 8 hours.

The inherent viscosity using chloroform as a solvent was 2.64 dl/g. The melting temperature and heat of fusion, as determined by differential scanning calorimetry, were 184.2° C. and 67.1 J/g, respectively.

EXAMPLE 10

Synthesis of 92/8 l-lactide/ε-caprolactone Copolymers

The reaction apparatus was comprised of a 1L stainless steel kettle with a 3-neck glass lid equipped with an overhead mechanical stirring unit vacuum adapter, and two 90° C. for an argon inlet. After obtaining a vacuum of 0.3 mm Hg, the apparatus was flame dried. An initial charge of 1124 grams (7.7966 moles) l-lactide was added to the kettle.

The apparatus and its contents were placed under room temperature vacuum for 1 hour. Using a high temperature oil bath, the apparatus and its contents were heated to 40° C. and kept under vacuum for 3 hours. The system was then purged with argon. The temperature of the oil bath was increased to 110° C. and stirring initiated at 32 rpm. Upon complete melting of the contents after 2.5 hours, a final charge consisting of 77.3 grams (0.678 moles) ε-caprolactone, 1.35 milliliters ($7.062 \times 10^{-3}$ moles) decyl alcohol, and 1.7 milliliters (3.389×10$^{-4}$ moles) of a 0.2M solution of stannous octoate catalyst in toluene was added to the kettle while stirring. After 20 minutes, the temperature was increased to 135° C. Stirring was stopped after 4.5 hours. The reaction was maintained at 135° C. for 72 hours. At the conclusion of this period, the polymer was isolated, ground, and then heated under reduced pressure (about 1 mm HG) for 4 hours at 37° C. and 8 hours at least 80° C.

The inherent viscosity using chloroform as a solvent was 2.72 dl/g. The melting temperature and heat of fusion, as determined by differential scanning calorimetry, were 182° C. and 59.9 J/g, respectively.

EXAMPLE 11

Synthesis of High Molecular Weight 95/5 l-lactide/ ε-caprolactone Copolymer

This copolymer is prepared using polymerization charges and conditions similar to those used in Example 9 with the exception of using a smaller amount of initiator (7.579×10$^{-3}$ mole, 1.45 ml) to obtain a higher molecular weight copolymer than the one of Example 9. The resulting copolymer is expected to have an inherent viscosity of more than 2.9 dl/g.

Comparative Example 12

Synthesis of High Molecular Weight 95/5 l-lactide/ glycolide Copolymer

This copolymer is prepared using polymerization charges and conditions similar to those used in Example 9 with the exception of substituting glycolide (0.421 mole, 4.63 g) for caprolactone and using a smaller amount of initiator (7.579×10$^{-3}$ mole, 1.45 ml) to obtain a higher molecular weight copolymer than the one of Example 6. The resulting copolymer is expected to have an inherent viscosity of more than 2.9 dl/g.

EXAMPLE 13

Synthesis of 91/9 l-lactide/ε-caprolactone Copolymer

This copolymer is prepared and characterized as described in Example 10, except using an initial ratio of l-lactide/ε-caprolactone of 91/9. The anticipated inherent viscosity and melting temperature of the polymer are about 2.60 dl/g and 178° C., respectively.

EXAMPLE 14

Synthesis of 91/19 l-lactide/trimethylene Carbonate Copolymer

The copolymer is prepared and characterized as described in Example 13, except substituting trimethylene carbonate for c-caprolactone, while maintaining an identical l-lactide mole fraction of an initial charge. The anticipated inherent viscosity and melting temperature are about 2.58 dl/g and 177° C., respectively.

EXAMPLE 15

Two-step Synthesis of a 91/9 l-lactide/ε-caprolactone Copolymer

Using a similar reaction and polymerization set-up as in Example 10, caprolactone (86.96 g, 0.7628 mole) is first polymerized in the presence of decyl alcohol (1.61 ml, 8.421×10$^-$mole) and stannous octoate as 0.2M solution in toluene (2.11 ml., 4.21×10$^{-4}$ mole) at 170° C. until 50% conversion is achieved (to be determined by a combination of NMR and GPC analysis in control runs). At this point, the temperature of the reaction mixture is lowered to 135° C. and l-lactide (1110.4 g, 7.7112 mole) is added. After the monomer melts, the temperature is maintained at 135° C. for 72 hours- the reaction mixture is stirred until it solidifies. At the conclusion of this period, the polymer is allowed to cool. The polymer is then isolated, ground, and purified as in Example 10. The anticipated inherent viscosity is about 1.55 dl/g.

EXAMPLE 16

Two-step Synthesis of a 91/9 l-lactide/trimethylene Carbonate Copolymer

The copolymer is prepared as in Example 15, except substituting trimethylene carbonate for ε-caprolactone, while maintaining an identical l-lactide mole fraction in the initial charge. The anticipated inherent viscosity is about 1.51 dl/g.

EXAMPLE 17

Comparative Analysis of Monofilaments Made of Different Copolymers Having Similar Inherent Viscosities To compare the effect of the type of minor monomeric repeat units (5%) on the properties of copolymers having 95% l-lactide-based sequences, the high molecular weight 95/5 l-lactide/glycolide copolymer of Example 12 and the high molecular weight 95/5 l-lactide/ε-caprolactone copolymer of Example 11 are converted to size 3-0 monofilament suture and their tensile and key suture properties are assessed. Although both polymers have the same inherent viscosities and hence, comparable molecular weights, the ε-caprolactone-containing copolymer yields monofilaments with more desirable suture properties as compared to its glycolide counterpart. More specifically, it is compliant, easy to tie down, has a higher knot strength, and knot security.

EXAMPLE 18

General Method for Multifilament Spinning and Yarn Orientation and Typical Yarn Properties Polymer was dried in an 80° C. vacuum oven for over 8 hours prior to extruding. A 1" single screw extruder with four zones was used to extrude the polymer into multifilament yarn. The polymer was extruded using a 50 filament die with 0.5 mm holes. Zone 1 was maintained at 210° C. Zone 2 was maintained at 214° C. Zone 3 was maintained at 216° C. Zone 4 was maintained at 220° C. The spin head was set at 220° C., while the feed roll and the draw roll were set at 30° C. The extruder was operated at 34 rpm, while the feed roll, draw roll, and relax roll were set at 210 rpm. The yarn can be drawn in two stages at a draw ratio of 4–5 X and 1.2–1.5 X using a heated drum at 105–110° C. and 110–120° C., respectively. Using these conditions, one can produce yarn with the following properties: tenacity=4–6.5 g/d and elongation=20–35.

TABLE I

Polymer Synthesis Conditions and Resulting Viscosity*
of Different Copolymers

| Polymer | Composition | M/I | M/C | Processing Conditions | Viscosity |
|---|---|---|---|---|---|
| Comp. Ex. 6 Lot 1 | 95/5 L/G | 1 000/1 | 20 000/1 | 130° C. for 48 hr. 120° C. for 16 hr. | 2.23$^c$ |
| Comp. Ex. 6 Lot 2 | 95/5 L/G | 850/1 | 20 000/1 | 140° C. for 48 hr. 120° C. for 17 hr. | 1.64 |
| Ex. 1 Lot 1 | 95/5 L/CL | 1 000/1 | 20 000/1 | 130° C. for 24 hr. 140° C. for 24 hr. 120° C. for 16 hr. | 2.60$^d$ |
| Ex. 1 Lot 2 | 95/5 L/CL | 1 000/1 | 20 000/1 | 140° C. for 48 hr. 120° C. for 16 hr. | 2.33 |
| Ex. 1 Lot 3 | 95/5 L/CL | 1 000/1 | 20 000/1 | 140° C. for 48 hr. 120° C. for 16 hr. | 2.72 |

$^a$Molar ratio of monomer/initiator.
$^b$Molar ratio of monomer/catalyst.
$^c$Viscosity run before final 16 hrs. of processing. Viscosity run in HFIP.
$^d$Viscosity run before final 16 hrs. of processing.
*Viscosities are measured in CHCl$_3$ or as otherwise indicated.

TABLE II

Extrusion Conditions and Extrudate Viscosity$^a$

| | Extrusion Temperature ° C. at | | | | Screw | Extrudate |
|---|---|---|---|---|---|---|
| Extrudate | Zone 1 | Zone 2 | Zone 3 | Die | Speed | η |
| Ex. 6 Lot 1 E1 | 153 | 151 | 176 | 177 | 30 to 35 | 1.47 |
| Ex. 6 Lot 1 E2 | 168 | 197 | 184 | 188 | 32 | — |
| Ex. 6 Lot 1 E3 | 153 | 193 | 186 | 189 | 35.7 | 1.1$^b$ |
| Ex. 1 Lot 1 B1 | 155 | 195 | 191 | 193 | 27.8 | 1.9 |

$^a$Viscosities (η) are run in CHCL$_3$ or as otherwise indicated.
$^b$Viscosity run in HFIP.

TABLE III-A

First-Stage Drawing Conditions for Fibers

| | Draw T- | Draw | Diameter * | |
|---|---|---|---|---|
| Fiber | (° C.) | Ratio | d$_o$ (mils) | d$_f$ (mils) |
| Ex. 6 Lot 1 E3 D1 | 70 | 2.6 | 19.7 | 7.5 |
| Ex. 6 Lot 1 E3 D2 | 75 | 2.9 | 19.7 | 6.7 |
| Ex. 1 Lot 1 E1 D1 | 75 | 2.2 | 25.6 | 11.4 |
| Ex. 1 Lot 1 El D2 | 75 | 2.4 | 25.6 | 10.6 |
| Ex. 1 Lot 1 E1 D3 | 75 | 2.4 | 25.6 | 10.6 |

* Diameter of unoriented (d$_0$) and oriented (d$_f$) monofilaments.

TABLE III-B

Tensile Properties of Partially Oriented Fibers*

| Fiber | d (mils) | Strength psi × 10$^{-3}$ | Modulus psi × 10$^{-3}$ | Elongation, % |
|---|---|---|---|---|
| Ex. 6 Lot 1 B3 D2 | 6.7 | 46.1 | 474.0 | 38.1 ± 5.0 |
| Ex. 1 Lot 1 E1 D3 | 10.6 | 44.9 | 431.8 | 33.4 ± 1.8 |

*Tested at 0.25 mm/sec using 1kN load cell; d = diameter of drawn monofilaments.

TABLE IV

Two-Stage Drawing of Example 1 Coploymer Extrudate and
Properties of Oriented Fibers*

| Material | Diameter (mm) | Draw Ratio | σ max psi × 10$^{-3}$ | E, psi × 10$^{-3}$ | E, (%) |
|---|---|---|---|---|---|
| Ex. 1 Lot 3 E1 D1 | 0.197 | 4.3 | 64.9 | 499.1 | 46.1 |
| Ex. 1 Lot 3 E1 D2 | 0.163 | 6.7 | 76.7 | 514.4 | 40.5 |
| Ex. 1 Lot 3 E1 D3 | 0.146 | 8.0 | 70.5 | 552.9 | 31.9 |

*The temperatures for the two-stage drawing were 70° C. and 85° C., respectively. σ = maximum tensile strength; E = Modulation; E = Elongation The foregoing description of preferred embodiments of the invention has been presented for illustration, and is not intended to be exhaustive. Modifications are possible in light of the above teachings or may be acquired from practice of the invention.

What is claimed is:

1. A crystalline copolymer comprising
    a copolymer of l-lactide and at least one cyclic monomer, said cyclic monomer comprising a liquid at or above about 40° C.,
    wherein the l-lactide derived sequences of the polymer chain comprise from about 86 to about 99 percent of all sequences, and
    wherein the copolymer has a T$_m$ of at least 150° C., exhibits a crystallinity of at least about 25%, and has an inherent viscosity of at least about 1.4 dl/g.

2. The copolymer set forth in claim 1 wherein the cyclic monomer comprises ε-caprolactone.

3. The copolymer set forth in claim 2 wherein the ε-caprolactone derived sequences of the polymer chain comprise from about 14 to about 5 percent of all sequences.

4. The copolymer set forth in claim 3 wherein the ε-caprolactone derived sequences of the polymer chain comprise about 8 percent of all sequences.

5. A monofilament suture made from the copolymer of claim 2 having an elastic modulus of greater than about 400,000 psi, a tensile strength of greater than about 40,000 psi, and a percent elongation of less than about 50%.

6. A multifilament yarn comprising the copolymer of claim 2.

7. A surgical suture comprising the multifilament yarn of claim 6.

8. A surgical device or construct comprising the multifilament yarn of claim 6 in the form of a mesh, a prosthetic tendon, a ligament or a vascular graft.

9. The copolymer set forth in claim 1 wherein the cyclic monomer comprises trimethylene carbonate.

10. The copolymer set forth in claim 9 further comprising ε-caprolactone derived polymer sequences.

11. A monofilament suture made from the copolymer of claim 9 having an elastic modulus of greater than about 400,000 psi, a tensile strength of greater than about 40,000 psi, and a percent elongation of less than about 50%.

12. A multifilament yarn comprising the copolymer of claim 9.

13. A surgical suture comprising the multifilament yarn of claim 10.

14. A surgical device or construct comprising the multifilament yarn of claim 12 in the form of a mesh, a prosthetic tendon, a ligament or a vascular graft.

* * * * *